United States Patent [19]

Miller

[11] Patent Number: 4,595,532

[45] Date of Patent: Jun. 17, 1986

[54] N-(SUBSTITUTED-METHYL)-AZETIDIN-2-ONES

[75] Inventor: Marvin J. Miller, South Bend, Ind.

[73] Assignee: University of Notre Dame du Lac, Notre Dame, Ind.

[21] Appl. No.: 718,127

[22] Filed: Apr. 1, 1985

Related U.S. Application Data

[63] Continuation of Ser. No. 463,101, Feb. 2, 1983, abandoned.

[51] Int. Cl.$^4$ .................. C07D 205/08; C07D 413/04; C07D 403/04; C07D 401/12
[52] U.S. Cl. .................. 260/239 A; 260/245.4; 260/330.3; 260/330.9; 544/316; 544/359; 546/275; 548/231
[58] Field of Search ............. 260/239 A, 245.4, 330.3, 260/330.9; 546/275; 544/316, 359

[56] References Cited

U.S. PATENT DOCUMENTS

| | | | |
|---|---|---|---|
| 4,207,234 | 6/1980 | Kamiya | 260/239 A |
| 4,322,345 | 3/1982 | Hirata et al. | 260/239 A |
| 4,337,197 | 6/1982 | Gordon et al. | 260/239 A |
| 4,397,784 | 8/1983 | Chu | 260/245.2 T |

FOREIGN PATENT DOCUMENTS

| | | |
|---|---|---|
| 0001715 | 5/1979 | European Pat. Off. . |
| 0017992 | 10/1980 | European Pat. Off. . |
| 0076621 | 4/1983 | European Pat. Off. . |
| 2006195 | 5/1979 | United Kingdom . |

OTHER PUBLICATIONS

Townsend et al., J.A.C.S. 103, 4582-3 (1981).
Townsend et al., Tetrahedron Letters 23, 4859 (1982).
Sheehan et al., J. Org. Chem. 38, 3034 (1973).
Sullivan et al., J. Organic Chem. 41, 1112.
Baer et al., J. Med. Chem. 16, 85.
Hakimelahi et al., Can. J. Chem. 59, 941 (1981).
Marchand-Brynaert et al., Tet Letters 1980, p. 3085.
J. Marchand-Brynaert et al., "Recent Advances in the Chemistry of Beta-Lactam Antibiotics", Second International Symposium, 1980, pp. 269-280.
Cossement et al., Tetrahedron Letters, vol. 24, No. 25, 1983, pp. 2563-2566.
Ghosez, et al., Tetrahedron Letters, vol. 39, No. 15, pp. 2493-2503.
Linkies et al., Tetrahedron Letters, vol. 21, No. 40, pp. 3869-3870.
Hakimelahi et al., Helv. Chim. Acta. vol. 65, No. 5, 1982, pp. 1374-1377.
Chemical Abstracts, vol. 98, p. 601 (1983).
Miller et al., "The Direct Chemical Conversion of Peptides to Beta-Lactams", Tetrahedron Letters, vol. 39, No. 15, pp. 2563-2570.

Primary Examiner—Mark L. Berch
Attorney, Agent, or Firm—William B. Scanlon; Arthur R. Whale

[57] ABSTRACT

N-Mono or N-disubstituted methyl-2-azetidinones are provided via cyclization of β-hydroxy or β-halo substituted acid sec-amides wherein the amide nitrogen is substituted with a mono- or di-substituted methyl group having activating substituents. Cyclization of β-hydroxy acid amides is mediated by triphenylphosphine-dialkylazodicarboxylate while cyclization of β-halo acid amides is mediated by strong bases e.g. lithium dialkylamides. E.g. Diethyl amino-protected L-serylaminomalonate is cyclized with 200 mole % TPP-diisopropylazodicarboxylate to N-(diethoxycarbonylmethyl)-3-protected-amino-2-azetidinone. The 2-azetidinones provided are useful intermediates.

18 Claims, No Drawings

N-(SUBSTITUTED-METHYL)-AZETIDIN-2-ONES

The invention described herein was made in the course of work under a grant or award from the Department of Health and Human Services.

This application is a continuation of application Ser. No. 463,101 filed Feb. 2, 1983, now abandoned.

BACKGROUND OF THE INVENTION

This invention relates to monocyclic $\beta$-lactam compounds and to a process for the preparation thereof. In particular, this invention relates to N-mono or di-substituted-methyl azetidin-2-ones and related compounds and to a method for the preparation thereof which comprises the cyclization of a $\beta$-hydroxy or $\beta$-halo N-mono or di-substituted-methyl amide. The compounds of the invention are useful intermediates in the preparation of monocyclic $\beta$-lactam antibiotics, $\beta$-lactamase inhibitors, and bicyclic $\beta$-lactam antibiotic compounds.

The class of $\beta$-lactam antibiotics includes the well-known penicillin and cephalosporin antibiotics. Newer types of $\beta$-lactam antiobiotics have been discovered of late, for example, thienamycin, nocardicin, clavulanic acid, isoclavulanic acid, and monobactam (Belgium Pat. No. 887,428). Because of the importance of the $\beta$-lactam antibiotics, there is a need for improved methods for their production and considerable research is being conducted to develop simple and economic routes of synthesis.

SUMMARY OF THE INVENTION

The monocyclic $\beta$-lactam compounds represented by the following general formula 1 are provided

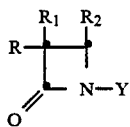

1 wherein R is preferably an amino or an acylamino group, $R_1$ and $R_2$ represent substituent groups, for example, lower alkyl, lower alkoxy and substituted alkyl groups, and Y represents a mono or di-substituted-methyl group wherein at least one of the substituent groups is an electron withdrawing group, or Y is a substituted vinyl group wherein one of the substituents is likewise an electron withdrawing group. This invention also provides a process for the preparation of the compounds of the formula 1 which comprises the cyclization of a $\beta$-hydroxy or $\beta$-halo-substituted amide represented by the following structural formula 2

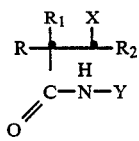

2 wherein Y is a mono or di-substituted-methyl group wherein either or both of the substituents are electron withdrawing groups such as the sulfo group or an esterified carboxy group, and X is hydroxy or halo. The process is carried out with a compound of the formula 2 wherein X is hydroxy with the complex formed with a dialkylazodicarboxylate and a phosphorus compound selected from triphenylphosphine, triphenylphosphite, diphenyl phenylphosphonate, and phenyldiphenylphosphinoate; and when X is halo such as chloro or bromo, cyclization is carried out with a lithium dialkylamide.

The compounds of the invention are useful intermediates in the synthesis of $\beta$-lactam antibiotics and $\beta$-lactamase inhibitors.

DETAILED DESCRIPTION

The monocyclic $\beta$-lactam compounds provided by this invention are N-mono or N-di-substituted-methyl azetidin-2-ones which can also be substituted in the 3- and 4-positions of the 4-membered ring as shown in the above structural formula 1. In particular, the terms R, $R_1$, $R_2$, and Y in the formula 1 are representative of the following groups:

R is hydrogen, $C_1$-$C_4$ alkoxy, amino, protected amino, acylamino, diacylamino, $C_1$-$C_4$ alkyl, or $C_1$-$C_4$ alkyl substituted by hydroxy, $C_1$-$C_4$ alkoxy, halogen, amino, protected amino, carboxy, or protected carboxy;

$R_1$ is hydrogen, hydroxy, $C_1$-$C_4$ alkoxy, halogen, or $C_1$-$C_4$ alkyl;

$R_2$ is hydrogen, phenyl, substituted phenyl, carboxy, $C_1$-$C_4$ alkoxycarbonyl, protected carboxy, sulfhydryl, $C_1$-$C_4$ alkylthio, $C_1$-$C_4$ alkyl, or $C_1$-$C_4$ alkyl substituted by hydroxy, $C_1$-$C_4$ alkoxy, halogen, amino or protected amino, carboxy or protected carboxy;

Y is a substituted-methyl group represented by the formulae

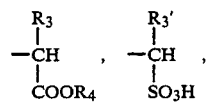

or a substituted vinyl group represented by the formula

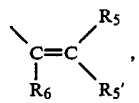

where in the above formulae $R_3$ and $R_3'$ are hydrogen, $C_1$-$C_4$ alkoxycarbonyl, protected carboxy, $C_1$-$C_4$ alkylsulfonyl, arylsulfonyl, $C_1$-$C_4$ alkylsulfinyl, arylsulfinyl, $C_1$-$C_4$ alkanoyl, aroyl, $C_1$-$C_4$ alkyl, cyano, vinyl, ethinyl;

$R_4$ is hydrogen, $C_1$-$C_4$ alkyl, or a carboxy protecting group;

$R_5$ and $R_5'$ are independently hydrogen, $C_1$-$C_4$ alkyl, phenyl, $C_1$-$C_4$ alkoxycarbonyl, or protected carboxy; and $R_6$ is hydrogen, $C_1$-$C_4$ alkyl, $C_1$-$C_4$ akoxycarbonyl, protected carboxy, or phenyl.

In the above definition of the compounds of the invention, $C_1$-$C_4$ alkoxy refers to methoxy, ethoxy, n-propoxy, iso-propoxy, n-butyloxy, and t-butyloxy; $C_1$-$C_4$ alkyl refers to the straight and branched chain $C_1$-$C_4$ alkyl groups such as methyl, ethyl, n-propyl, iso-propyl, n-butyl, sec-butyl, and t-butyl; halogen refers to fluoro, chloro, bromo, and iodo; $C_1$-$C_4$ alkyl substituted by hydroxy, $C_1$-$C_4$ alkoxy, halogen, amino, protected amino, carboxy, or protected carboxy refers to the hydroxy-substituted lower alkyl groups, for example, hydroxymethyl, 2-hydroxyethyl, 1-hydroxyethyl, 3-hydroxypropyl, 2-hydroxybutyl, and like hydroxy-substituted alkyl groups; $C_1$-$C_4$ alkyl substituted by $C_1-C_4$ alkoxy refer to such groups as, for example, methoxymethyl, ethoxymethyl, 2-methoxyethyl, 2-ethoxyethyl, t-butyloxymethyl, and like either groups; halo-substituted $C_1-C_4$ alkyl refers to iodomethyl, bromomethyl, fluoromethyl, 2-chloroethyl, 2-bromoethyl, 3-chloropropyl, and like haloalkyl groups; $C_1-C_4$ alkyl substituted by amino refers to the lower aminoalkyl radicals such as aminomethyl, 2-aminoethyl, 3-aminopropyl, 2-aminopropyl, 3-aminobutyl, and like substituted groups; $C_1-C_4$ alkyl substituted by protected amino refers to amino-substituted $C_1-C_4$ alkyl groups such as those mentioned above wherein the amino group is protected by a conventional amino protecting group such as an alkoxycarbonyl or cycloalkoxycarbonyl group, a benzyloxycarbonyl or substituted benzyloxycarbonyl group, an enamine protecting group, or a cleavable acyl group such as chloroacetyl, dichloroacetyl, and the like; carboxy-substituted $C_1-C_4$ alkyl refers to carboxymethyl, 2-carboxyethyl, 3-carboxypropyl, 2-carboxypropyl, 4-carboxybutyl, and like groups; while $C_1-C_4$ alkyl substituted by protected carboxy refers to carboxy-substituted lower alkyl groups such as those mentioned above and wherein the carboxy group is protected by conventional carboxy-protecting groups such as, for example, benzyl or substituted benzyl, diphenylmethyl or substituted diphenylmethyl, substituted alkyl such as trichloroethyl, 2-iodoethyl, phenacyl, trialkylsilyl, and t-butyl; $C_1-C_4$ alkoxycarbonyl refers to methoxycarbonyl, ethoxycarbonyl, n-propoxycarbonyl, t-butoxycarbonyl, n-butoxycarbonyl, and like lower alkoxycarbonyl groups.

The term sulfhydryl refers to the —SH group while $C_1-C_4$ alkylthio refers to alkyl-S-groups such as methylthio, ethylthio, propylthio and butylthio.

"$C_2-C_4$ Alkanoylthio" refers to

groups such as acetylthio, propionylthio and the like.

The term "substituted phenyl" refers to phenyl substituted by $C_1-C_4$ alkyl, $C_1-C_4$ alkoxy, carboxy, protected carboxy, hydroxy, halogen, or cyano.

The term "$C_1-C_4$ alkanoyl" refers to formyl, acetyl, propionyl, butyryl, and like acyl groups.

Representative of the 3-acylamino groups (formula 1, R is acylamino) are the acyl groups derived from carboxylic acids, in particular the acyl groups at the 7-position of the cephalosporin and the 6-position of the penicillin antibiotics. In particular, the acyl group of the acylamino group, $R_1$ is $C_1-C_5$ alkanoyl, substituted $C_2-C_5$ alkanoyl substituted by halogen, cyano, or hydroxy; an arylacetyl or heteroarylacetyl group represented by the formula

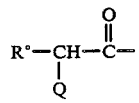

wherein R° is thienyl, benzothienyl, furyl, benzofuryl, thiazolyl, oxazolyl, isoxazolyl, isothiazolyl, pyrazolyl, thiadiazolyl, oxadiazolyl, pyridyl, and said heterocyclic rings substituted by $C_1-C_4$ alkyl, amino, protected amino, or hydroxy; cyclohexadienyl, naphthyl, phenyl, or a substituted phenyl group represented by the formula

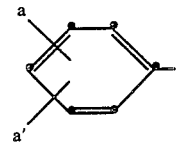

wherein a and a' independently are hydrogen, halogen, hydroxy, $C_1-C_4$ alkyl, $C_1-C_4$ alkoxy, amino, aminomethyl, methylsulfonylamino, hydroxymethyl, trifluoromethyl, carboxy, protected carboxy, carboxymethyl, or protected carboxymethyl; Q is hydrogen, hydroxy, $C_1-C_4$ alkanoyloxy, carboxy, protected carboxy, sulfo(—SO$_3$H), amino, protected amino, or a substituted amino group represented by the formula

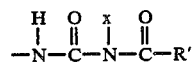

wherein R' is furyl, thienyl, phenyl, halophenyl, nitrophenyl, styryl, halostyryl, nitrostyryl; or a group of the formula

wherein R'' is hydrogen, $C_1-C_4$ alkyl, benzyl, $C_2-C_5$ alkanoyl, or $C_1-C_3$ alkylsulfonyl; and x and y when taken separately are hydrogen or $C_1-C_3$ alkyl, and when taken together form a 5- or 6-membered ring represented by the formula

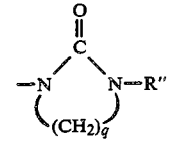

wherein R'' has the same meanings as defined hereinabove and q is 2 or 3; or Q is a substituted amino group represented by the formula

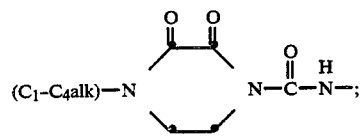

or Q is a benzamido group represented by the formula

wherein b' is an integer of from 1-3; or R is an acylamino group of the formula

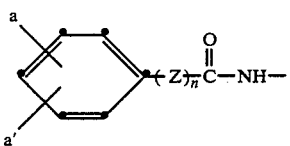

wherein a and a' have the same meanings as defined above, Z is O or S, and n is 0 or 1; or an oximino-substituted acylamino group represented by the formula

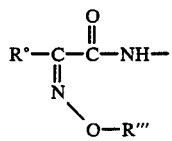

wherein R° is as defined above, and R''' is hydrogen, $C_1$–$C_4$ alkyl, or a carboxy-substituted alkyl or cycloalkyl group represented by the formula

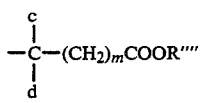

wherein m is 0–3, and c and d when taken separately are independently hydrogen or $C_1$–$C_3$ alkyl, and when taken together with the carbon atom to which they are bonded form a 3 to 6-membered carbocyclic ring; and wherein R'''' is hydrogen, $C_1$–$C_4$ alkyl, or a carboxy-protecting ester forming group.

When R in the above formula 1 is a diacylamino group, R represents a group of the formula

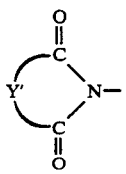

wherein Y' is $C_1$–$C_3$ alkylene or o-phenylene. Examples of diacylamino groups represented by the above formula are phthalimido, succinimide, maleimido, and like cyclic diacylamino groups.

When R in the formula 1 is a protected-amino group, R is an amino group substituted by a conventional amino-protecting group used in the art for the temporary protection of an amino group. Examples of such conventional protecting groups are, for example, the alkyloxycarbonyl, substituted alkoxycarbonyl, cycloalkoxycarbonyl, bicyclicalkyloxycarbonyl, alkenyloxycarbonyl, arylalkyloxycarbonyl, and like groups. Examples of such protecting groups are ethoxycarbonyl, cyclopentyloxycarbonyl, cyclohexyloxycarbonyl, 2,2,2-trichloroethoxycarbonyl, allyloxycarbonyl, 1-adamantyloxycarbonyl, t-butyloxycarbonyl, t-amyloxycarbonyl, benzyloxycarbonyl (Cbz), p-nitrobenzyloxycarbonyl, p-methoxybenzyloxycarbonyl, diphenylmethoxycarbonyl, and the like. Other protecting groups are the trialkylsilyl-protecting groups such as trimethylsilyl, and the bis-trialkylsilyl-protecting groups, such as N,N-bis-trimethylsilyl, and the like. Other convenient amino-protecting groups are the phthaloyl group and the formyl group. An especially preferred amino-protecting group of this invention is the 4,5-diphenyl-4-oxazolin-2-one group formed with the amino group and 1,2-diphenylvinylene carbonate (J. C. Sheehan, et al., *J. Org. Chem.*, 18, No. 17, 3034–3040 [1973]).

The amino-protecting group serves as a blocking group for the temporary protection of the amino group in the 3-position of the azetidinone ring during the process for the preparation thereof as described hereinafter. In particular, the 3-amino group is protected to prevent competitive amide formation in the process of the invention.

The term carboxy-protecting group as employed in the definition of the compounds represented by formula 1 refers to conventional carboxylic acid-protecting ester groups commonly used in the β-lactam art for the temporary protection of the carboxylic acid function. These esters are well known for their ease of preparation and removal. The carboxylic acid protecting ester groups function to block the carboxylic acid function during the process of this invention to prevent the formation of side products as well as to direct the occurrence of the reaction at the desired carboxylic acid function when two or more are present in the same molecule eg. the compound of formula 2. Examples of such ester groups are t-butyl, trihaloethyl esters such as the 2,2,2-trichloroethyl ester, allyl, 2-iodoethyl, methoxymethyl, esters formed with tertiary ethinyl carbinols, such as dimethylethinylcarbinol, diethylethinylcarbinol, 1-ethinylcyclopentanol, 1-ethinylcyclohexanol, and like carbinols; the arylalkyl ester forming groups such as benzyl and substituted benzyl, for example, p-nitrobenzyl, p-methoxybenzyl, p-methylbenzyl, diphenylmethyl, 4-methoxydiphenylmethyl, and like protecting groups; the trialkylsilyl esters such as trimethylsilyl and the like, and other conventional carboxy-protecting ester groups.

Examples of substituted methyl groups represented by Y in the structural formula 1 when Y is a group —CH($R_3$)COOR$_4$, are carboxymethyl, methoxycarbonylmethyl, ethoxycarbonylmethyl, benzyloxycarbonylmethyl, dicarboxymethyl, diethoxycarbonylmethyl, methylsulfinylcarboxymethyl, benzolycarboxymethyl, p-nitrobenzoylcarboxymethyl, cyanocarboxymethyl, acetylcarboxymethyl, acetylethoxycarbonylmethyl, phenylsulfonylcarboxymethyl, methylsulfinylcarboxymethyl, phenylsulfinylcarboxymethyl, 1-carboxyethyl, 1-ethoxycarbonylethyl, 3-carboxypropenyl, 3-carboxypropynyl, and like carboxy-substituted methyl groups. Examples of substituted methyl groups represented by Y when Y is a substituted sulfomethyl group represented by the radical —CH($R_3$)SO$_3$H, are sulfomethyl, 1-sulfoethyl, 1-sulfopropyl, 1-sulfopropenyl, 1-sulfopropynyl, carboxysulfomethyl, ethoxycarbonylsulfomethyl, acetylsulfomethyl, and like substituted and unsubstituted sulfomethyl groups. Representative of the substituted methyl groups when Y in the above formula 1 is a substituted vinyl group are 2-phenylvinyl (styryl), 1-carboxyvinyl, 2-carboxyvinyl, 1-ethoxycarbonylvinyl, 2,2-diethoxycarbonylvinyl, 1-ethoxycarbonyl-2,2-diphenylvinyl, 1,2-dimethyl-2-phenylvinyl, 2-phenyl-2-ethoxycarbonylvinyl, and like substituted vinyl groups.

The compounds of the invention represented by the formula 1 wherein a free amino or free carboxy group is present can be in salt form. For instance when R represents amino, the acid addition salts are formed with suitable acids, for example, hydrochloric acid, sulfuric acid, hydrobromic acid, trifluoroacetic acid, formic acid, and like acids. Likewise, any free carboxy group can be in the salt form such as, for example, the sodium salt, the potassium salt, the ammonium salt, and salts formed with basic amines, for example, the lower alkyl primary, secondary, and tertiary amines such as diethylamine, ethylamine, methylamine, dicyclohexylamine, hexylamine, ethanolamine, diethanolamine, and like amines. Such salts may be useful in the isolation and purification of the compounds of the invention.

Compounds represented by the formula 1 wherein R is a free amino group are more stabile in salt form and accordingly are stored for future use in the salt form. The hydrochloride salt is a preferred salt form of the 3-aminoazetidinones.

Examples of compounds of the invention represented by the formula 1 wherein R is an amino group include the following.

N-(ethoxycarbonylmethyl)-3-amino-2-azetidinone,
N-[(diethoxycarbonyl)methyl]-3-amino-2-azetidinone,
N-[(diethoxycarbonyl)methyl]-3-amino-4-methyl-2-azetidinone,
N-(carboxymethyl)-3-aminoazetidinone,
N-(diethoxycarbonylmethyl)-3-amino-4-carboxy-2-azetidinone,
N-(diethoxycarbonylmethyl)-3-amino-4-hydroxymethyl-2-azetidinone,
N-(2-methyl-1-ethoxycarbonylpropen-1-yl)-3-amino-2-azetidinone,
N-(1-ethoxycarbonylpropene-2-yl)-3-amino-2-azetidinone,
N-(sulfomethyl)-3-amino-2-azetidinone,
N-(cyanoethoxycarbonylmethyl)-3-amino-4-ethyl-2-azetidinone,
and the acid addition salts thereof.

Examples of compounds of the invention represented by the formula 1 wherein R is a protected-amino group are the following:

N-(diethoxycarbonylmethyl)-3-phthalimido-2-azetidinone,
N-(dibenzyloxycarbonylmethyl)-3-phthalimido-2-azetidinone,
N-[di(4-nitrobenzyloxycarbonyl)methyl]-3-benzyloxycarbonylamino-2-azetidinone,
N-[di(diphenylmethoxycarbonyl)methyl]-3-adamantyloxycarbonylamino-4-methyl-2-azetidinone,
N-(diethoxycarbonylmethyl)-3-(4,5-diphenyl-4-oxazolin-2-one-3-yl)-2-azetidinone,
N-[di(4-nitrobenzyloxycarbonyl)methyl]-3-(4,5-diphenyl-4-oxazolin-2-one-3-yl)-2-azetidinone,
N-(dibenzyloxycarbonylmethyl)-3-(4,5-diphenyl-4-oxazolin-2-one-3-yl)-4-diphenylmethoxycarbonyl-2-azetidinone,
N-(diphenylmethoxycarbonylmethyl)-3-(4,5-diphenyl-4-oxazolin-2-one-3-yl)-2-azetidinone,
N-(sulfomethyl)-3-(4,5-diphenyl-4-oxazolin-2-one-3-yl)-4-hydroxyethyl-2-azetidinone, and
N-(1-ethoxycarbonyl-2-methylpropene-1-yl)-3-(4,5-diphenyl-4-oxazolin-2-one-3-yl)-3-chloromethyl-2-azetidinone.

Examples of compounds represented by the formula 1 wherein R is an acylamino group include N-(carboxymethyl)-3-phenylacetamido-2-azetidinone,
N-(carboxymethyl)-3-phenoxyacetamido-2-azetidinone,
N-(diethoxycarbonylmethyl)-3-benzamido-2-azetidinone N-(sulfomethyl)-3-(4-methylbenzamido)-4-methyl-2-azetidinone,
N-(sulfocarboxymethyl)-3-(2-thienylacetamido)-2-azetidinone,
N-(1-methyl-2-carboxyvinyl)-3-($\alpha$-carboxyphenylacetamido)-2-azetidinone,
N-(dibenzyloxycarbonylmethyl)-3-($\alpha$-sulfophenylacetamido)-2-azetidinone,
N-(t-butyloxycarbonylmethyl)-3-formamido-4-carboxy-2-azetidinone,
N-(1-ethoxycarbonyl-2-methylpropen-1-yl)-3-methoxy-3-(2-thienylacetamido)-4-methyl-2-azetidinone,
N-(carboxymethyl)-3-($\alpha$-hydroxyphenylacetamido)-2-azetidinone,
N-(carboxymethyl)-3-($\alpha$-aminophenylacetamido)-2-azetidinone,
N-(sulfomethyl)-3-[2-(2-aminothiazol-4-yl)-2-methoxyiminoacetamido]-4-methyl-2-azetidinone,
N-sulfomethyl-3-[2-(4-hydroxyphenyl)-2-(4-ethylpiperazine-2,3-dione-1-yl)carbonylamino]-2-azetidinone,
N-(carboxymethyl)-3-[2-(phenyl)-2-(2,4-dihydroxybenzamido]-2-azetidinone,
N-(sulfomethyl)-3-[2-(2-furyl)-2-methoxyiminoacetamido]-2-azetidinone,
N-(sulfomethyl)-3-[2-(4-hydroxyphenyl)-2-(3-methylcarbamoyl-3-methylureido)acetamido]-2-azetidinone,
N-(1-methyl-2,2-diethoxycarbonylvinyl)-3-cyanoacetamido-4-carboxy-2-azetidinone,
N-(1-sulfoprop-1-yl)-3-(3,4-dichlorophenylmercaptoacetamido)-2-azetidinone,
N-(1-carboxyethyl)-3-acetamido-2-azetidinone,
N-3-ethoxycarbonylbutine-3-yl)-3-phenylacetamido-2-azetidinone,
N-(carboxymethyl)-3-[2-(2-aminothiazol-4-yl)-2-methoxyiminoacetamido]-2-azetidinone,
N-(diethoxycarbonylmethyl)-3-[2-(2-aminothiazol-4-yl)-2-methoxyiminoacetamido]-3-methyl-2-azetidinone,
N-[di(4-nitrobenzyloxycarbonyl)methyl]-3-[2-(2-tritylaminothiazol-4-yl)-3-(4-nitrobenzyloxycarbonyl)-2-azetidinone, and
N-(carboxymethyl)-3-[2-(2-aminothiazol-4-yl)-2-(2-carboxyprop-2-yl)oxyiminoacetamido]-2-azetidinone.

The compounds of the invention (formula 1) are obtained by the novel process of this invention. According to the process a $\beta$-hydroxy or $\beta$-halocarboxylic acid represented by the formula

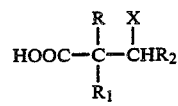

wherein X is hydroxy or halo, is converted to the substituted amide represented by the formula 2

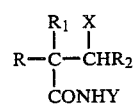

with the amine $H_2N$—Y. The substituted amide is then cyclized to the $\beta$-lactam, a 2-azetidinone represented by the formula 1.

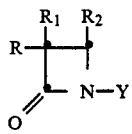

In the above formulae R, $R_1$, $R_2$, X, and Y have the same meanings as defined hereinabove for formula 1.

The substituted amide 2 is prepared by reacting the amine $NH_2Y$ with an active derivative of the carboxylic acid such as an acid halide, acid azide, acid anhydride, or a so-called active ester. Acid halides such as the acid chloride or acid bromide are reacted with the amine at ordinary temperatures in an inert solvent in the presence of an acid binding agent, e.g. triethylamine. When R in the above formula is a protected-amino, acylamino, or diacylamino group, an active ester is preferably used to form the substituted amide. Active esters such as those formed with N-hydroxyimides e.g. N-hydroxysuccinimide and N-hydroxyphthalimide, and with N-hydroxybenzotriazole (HBT) can be used in the process. A preferred active ester is the HBT ester. Active esters prepared with the acid and methyl chloroformate or isobutyl chloroformate can also be used.

In preparing the substituted amides of formula 2 wherein R is a protected-amino, acylamino or diacylamino group, the protected amino acid, HBT, the amine $NH_2Y$, and a carbodiimide are reacted in an inert solvent such as methylene chloride, dimethylformamide, dimethylacetamide or acetonitrile. The carbodiimide condenses the protected amino acid with the HBT to form the active ester which then reacts with the $H_2NY$ amine to form the substituted amide. Carbodiimides such as the water insoluble dicyclohexylcarbodiimide can be used, alternatively, a water soluble carbodiimide such as 1-cyclohexyl-3-(2-morpholinoethyl)carbodiimide metho-p-toluene sulfonate can be used.

The primary amines, $H_2NY$, used to prepare the substituted amides 2 are represented by the formulae.

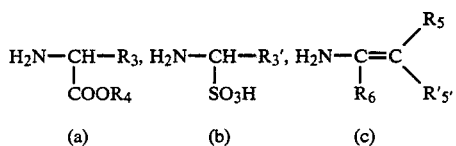

Examples of the amines employed in the process include ethyl glycinate, methyl glycinate, ethyl cyanoglycinate, p-methoxybenzyl glycinate, p-nitrobenzyl glycinate, diphenylmethyl glycinate, diethyl aminomalonate, dimethyl aminomalonate, ethyl-2-amino-3-oxobutyrate, ethyl α-sulfoglycinate, ethyl α-benzoylaminoglycinate, ethyl α-aminopropionate, aminomethanesulfonic acid, ethyl 3-aminocrotonate, and dehydrovaline.

Examples of α-substituted acids used in the process are the amino acids, serine, threonine, β-hydroxyglutamic acid, β-hydroxylysine, β-hydroxyaspartic acid, wherein the amino group is suitably protected, and the β-substituted acids; malic acid, chloro and bromo succinic acid, chloropivalic acid, bromopivalic acid, α-methoxy-β-hydroxybutyric acid, tartaric acid, α,β-dihydroxyhexanoic acid, α-(2-hydroxyethyl)-β-hydroxybutyric acid, and the like acids.

The cyclization of the substituted amide 2, to the azetidinone 3, wherein X is hydroxy and Y is a sulfomethyl, esterified carboxymethyl, or substituted vinyl group formed with amines a, b, or c is carried out in an inert anhydrous solvent with an organo phosphorous compound selected from triphenylphosphine, triphenylphosphite, diphenyl phenylphosphonate, and phenyl diphenylphosphinoate, and a dialkylazodicarboxylate. The cyclization occurs readily under mild conditions, for example, at a temperature between about 15° C. and about 40° C. and conveniently at or about ambient room temperature. The organo phosphorous compound and the dialkylazodicarboxylate are each used in about 100 mole percent to about 150 mole percent relative to the substituted amide 2. Solvents which can be used are desirably the lower boiling aprotic organic solvents in which the starting material and the reactants are soluble. Tetrahydrofuran (THF) is a preferred solvent while other common solvents such as acetonitrile, diethyl ether, ethyl acetate, methylene chloride, dimethylformamide, and dimethylacetamide may be used as well as mixtures of such organic solvents. THF is a preferred solvent because of its ease of removal from the reaction mixture. Preferred dialkylazodicarboxylates are diethylazodicarboxylate and diisopropylazodicarboxylate.

A preferred organo phosphorus compound is triphenylphosphine. The cyclization is carried out by adding the dialkylazodicarboxylate to a solution of the substituted amide 2 and the organo phosphorus with agitation. The cyclization is usually complete in about one hour or less when the process is conducted on a small scale with the preferred triphenylphosphine. For large scale manufacturing the reaction should be completed in somewhat longer times.

In an example of the process N-benzyloxycarbonyl L-serine is coupled with diethylaminomalonate to form the dipeptide (substituted amide 2 wherein R is protected-amino, $R_1=R_2=R_3=H$, and Y is $-CH(COOC_2H_5)$. The dipeptide is reacted with triphenylphosphinediethylazodicarboxylate to form the azetidinone N-(diethoxycarbonylmethyl)-3-benzyloxycarbonylamino-2-azetidinone and a minor amount of the aziridine side product as shown in the following reaction scheme.

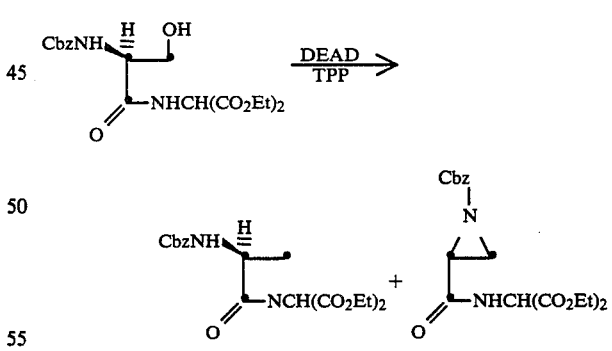

In carrying out the process it will be appreciated that any free carboxy groups, other than that required to form the desired amide with $H_2NY$, are protected during the process with a conventional carboxy-protecting ester group. Likewise any free amino groups, such as when R is amino, are protected with an amino-protecting group during the process.

When the process is carried out with a β-halo substituted amide (formula 2, X=halo), the cyclization to the β-lactam 3 is effected with a strong base such as a lithium dialkylamide eg. lithium di-tert-butylamide, lithium diisopropylamide and like lithium amides or lithium hexamethyldisilazide. The cyclization is carried out under anhydrous conditions in an inert aprotic organic solvent such as THF, dimethylformamide or dimethylacetamide. Mixtures of such solvents may also be used to form the reaction medium.

A preferred base is a lithium dialkylamide and, in particular lithium diisopropylamide. With the preferred base the reaction is carried out initially at a temperature between about −80° C. and about −25° C. at which temperature the anionic form of the substituted amide is generated. Thereafter the reaction is allowed to warm to a temperature of between about 10° C. and about 25° C. during which $\beta$-lactam ring formation occurs. Approximately 200 mole percent of a preferred base relative to the substituted amide is used for best yields of the $\beta$-lactam compound. When used at 100 mole percent the desired $\beta$-lactam product is obtained in only minor amounts, and in the instance wherein Y is a sulfo-substituted methyl group or an esterified carboxy-substituted methyl group (formed with amines a and b), the substituted pyrrolidone-2 is the major product isolated.

According to the process of this invention a selective cyclization to the 4-membered $\beta$-lactam ring is realized. N-alkylation of the amide nitrogen of the $\beta$-substituted amide (formula 2) occurs rather than C-alkylation of the $\alpha'$-carbon bearing the electron withdrawing group(s). C-Alkylation of the active methylene group would be expected since the acidity of the amide N—H bond and the $\alpha'$—CH bond should differ only slightly. For example, cyclization via C-alkylation of Cbz-protected serylaminomalonate represented by the formula

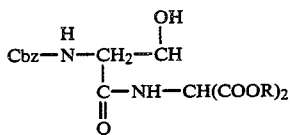

would yield the 5-membered pyrrolidone-2 represented by the formula

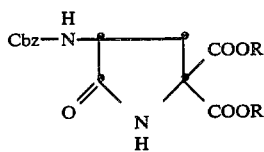

It has been found, however, that the greater the acidity of the $\alpha'$—CH proton the more selective the amide N—H alkylation becomes and the more the 4-membered $\beta$-lactam product predominates.

The preferred process of this invention for the preparation of the $\beta$-lactam compounds of formula 1 shown below

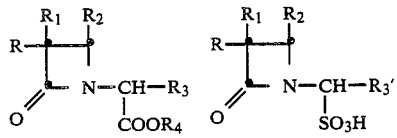

is the cyclization of a $\beta$-hydroxy substituted amide 2 (X=OH) with triphenylphosphine and a dialkylazodicarboxylate.

A further preferred embodiment of the process for the preparation of a compound of the formula 1 wherein Y is a group of the formula

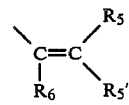

comprises the cyclization of a $\beta$-halo substituted amide 2.

A further preferred process of this invention comprises the use of a $\beta$-hydroxy substituted amide represented by the formula

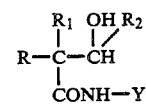

wherein R is protected-amino, acylamino, or diacylamino, and the cyclization thereof to a 3-protected-amino-, acylamino-, or diacylamino-2-azetidinone. In particular, R is a protected-amino group in the process and Y is a group represented by the formulae.

Preferred protected-amino groups in this embodiment of the invention are the carbamate protecting groups as defined hereinabove and in particular the benzyloxycarbonylamino and p-nitrobenzyloxycarbonylamino protected-amino groups. A particularly preferred protected-amino group is the 4,5-diphenyl-4-oxazolin-2-one group ("Ox" protecting group) represented by the formula.

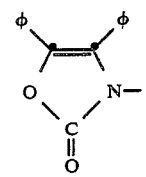

In a further preferred embodiment R is a preferred amino-protected amino group and $R_3$ is hydrogen, $C_1-C_4$ alkoxycarbonyl, or protected-carboxy, and $R_4$ is $C_1-C_4$ alkyl or a carboxy protecting group. In an example of the preferred embodiment N-Cbz-L-serine is converted to the active HBT ester with HBT and dicyclohexylcarbodiimide and the ester allowed to react with diethyl aminomalonate to form the N-Cbz-L-serineaminomalonate dipeptide represented by the formula

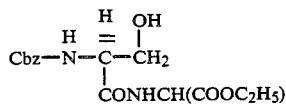

The dipeptide is reacted with 100 mole percent of TPP and about 100 mole percent of diethylazodicarboxylate to provide the $\beta$-lactam product, N-[(diethoxycarbonyl)methyl]-3-benzyloxycarbonylamino-2-azetidinone and the aziridine side product as shown in the following reaction scheme,

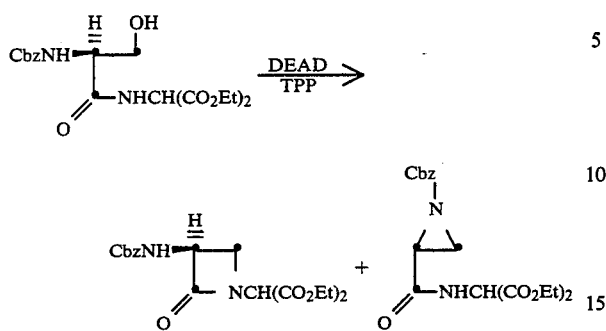

wherein Cbz=benzyloxycarbonyl; DEAD=diethylazodicarboxylate, and TPP=triphenylphosphine. The mixture is separated by chromatography to provide the purified β-lactam compound.

In another preferred embodiment of the invention L-serine is reacted with 1,2-diphenylvinylene carbonate to provide the Ox protected-L-serine and the latter is converted to the HBT ester and coupled with diethyl aminomalonate to form the dipeptide (formula 2, R=protected-amino, X=OH, $R_1=R_2=H$, and Y=diethoxycarbonylmethyl). The Ox protected dipeptide is reacted with TPP and diisopropylazodicarboxylate (DIAD) to provide the 3-Ox-protected-amino β-lactam as shown in the following reaction scheme.

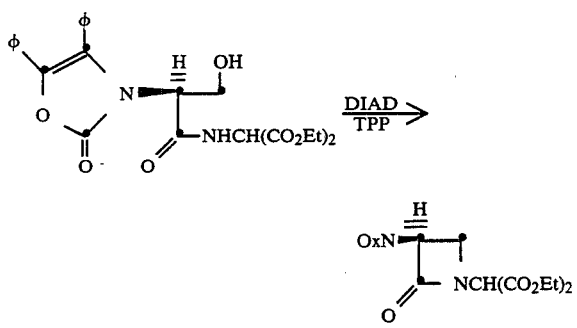

In a further preferred embodiment of the invention L-threonine is converted to the Ox-protected derivative, coupled with diethyl aminomalonate and, the dipeptide obtained is converted with TPP and diisopropylazodicarboxylate to the Ox-protected 3-amino-2-azetidinone as shown in the following reaction scheme.

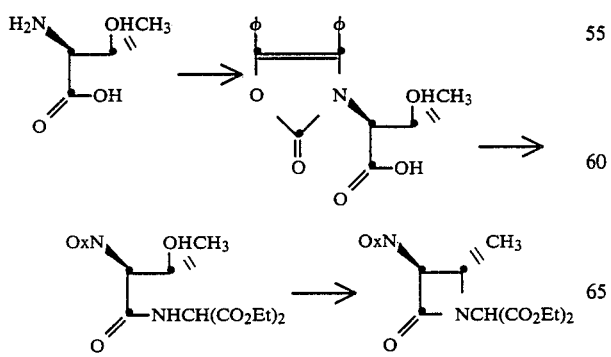

The amino-protecting group of the 3-protected amino-2-azetidinones is removed to provide the 3-amino-2-azetidinones. For example in the above preferred embodiments the Cbz protecting group is removed by hydrogenolysis using palladium on carbon catalyst. The Ox protecting group is removed likewise as shown below.

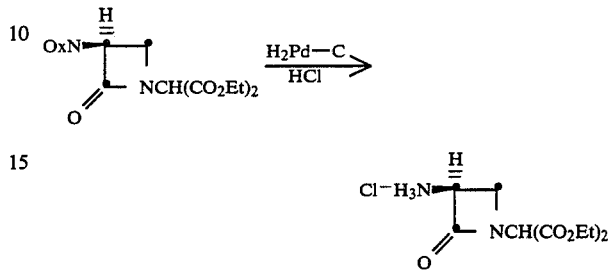

The 3-amino-2-azetidinones (formula 1, R=NH₂), can be acylated with the active derivative of the desired carboxylic acid to provide the compounds of formula 1 wherein R is an acylamino group.

Alternatively, the 3-acylamino-2-azetidinones (formula 1) can be obtained in the process of the invention as described hereinabove. However, in the process an acylamino-substituted amide (formula 2, R=acylamino) undergoes cyclization to form the oxazoline side product as well as β-lactam formation. Accordingly, the 3-acylamino-2-azetidinones are preferably prepared via acylation of a 3-amino-2-azetidinone obtained with a 3-protected-amino-azetidinone as described above.

Preferred 3-acylaminoazetidinones of the invention are represented by the formula 1 wherein R is amino, protected-amino or an acylamino group. Further preferred 3-acylamino-2-azetidinones are represented by the formula

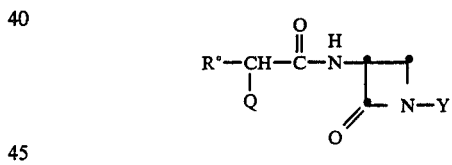

wherein Y is —CH₂COOH or —CH₂SO₃H.

Examples of such preferred compounds are N-carboxymethyl-3-phenylglycylamino-2-azetidinone, N-sulfomethyl-3-mandeloylamino-2-azetidinone, N-carboxymethyl-3-(2-thienylacetylamino)-2-azetidinone, N-carboxymethyl-3-mandeloylamino-2-azetidinone, N-sulfomethyl-3-mandeloylamino-2-azetidinone, N-carboxymethyl-3-(α-carboxyphenylacetylamino)-2-azetidinone, N-carboxymethyl-3-[α-carboxy-(4-hydroxyphenyl)acetylamino]-2-azetidinone, N-sulfomethyl-3-(α-sulfophenylacetylamino)-2-azetidinone and N-carboxymethyl-3-(α-sulfophenylacetylamino)-2-azetidinone.

A further preferred group of compounds of the invention are represented by the following formula

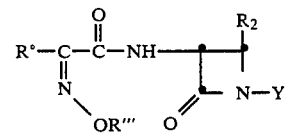

wherein Y is carboxymethyl or sulfomethyl and $R_3$ and $R_4$ independently are hydrogen or methyl, and R° and R''' have the same meanings as defined for formula 1. Preferably R° is 2-furyl, 2-thienyl, or 2-aminothiazol-4-yl, and R''' is methyl, carboxymethyl, or 2-carboxyprop-2-yl. Examples of the preferred compounds are N-sulfomethyl-3-[2-(2-aminothiazol-4-yl)-2-methoxyiminoacetamido]-4-methyl-2-azetidinone, N-sulfomethyl-3-[2-(2-aminothiazol-4-yl)-2-(2-carboxyprop-2-yl)oxyiminoacetamido]-4-methyl-2-azetidinone, N-carboxymethyl-3-[2-(2-aminothiazol-4-yl)-2-methoxyiminoacetamido]-2-azetidinone, N-carboxymethyl-3-[2-(2-furyl)-2-methoxyiminoacetamido]-4-methyl-2-azetidinone, N-carboxymethyl-3-[2-(2-thienyl)-2-(2-carboxyprop-2-yl)oxyiminoacetamido]-2-azetidinone, and the sodium and potassium salts thereof.

The $\beta$-lactam compounds represented by the formula 1 are intermediates useful in the preparation of antibiotics and $\beta$-lactamase inhibitors. A number of preparative routes have been devised for the penem, penam, oxapenem, oxacephalosporins, clavulanic acid, monobactam, and thienomycin structures, virtually all of which employ a substituted 2-azetidinone. The compounds (formula 1) of this invention can be used in such preparative routes or can be converted by methods known in the art to structures which in turn can be used as intermediates. For example, in mentioning only a few of such routes, compounds of the formula 1 wherein $R_1$ is hydrogen, $R_2$ is carboxy, and Y is a carboxy protected carboxymethyl group can be converted to the 2-substituted penams via the corresponding 4-methylthio-2-azetidinones as described by Foxton, M. W. et al., "Recent Advances in the Chemistry of $\beta$-lactam Antibiotics", G. I. Gregory (ed), 1981 p. 281; and *Tetrahedron Letters*, 1981, 22, 2479.

Likewise, the 2-substituted penems described by Woodward, R. B. et al., *J. Amer. Chem. Soc.*, 1978, 100, 8214, can be prepared via the 4-acylthio-2-azetidinones obtained by known methods with compounds of the invention.

Compounds of the invention wherein R is hydroxy-substituted alkyl (eg. ethyl) and Y is a carboxy substituted vinyl group can be used in the preparation of thienamycin described by Karady, S. et al., *J. Amer. Chem. Soc.*, 1981, 103, 6765, or the method described by Schmitt, S. M. et al., *J. Org. Chem.* 1980, 100, 313.

The compounds wherein Y is a substituted vinyl group can be converted by known oxidative cleavage methods, eg. with ozone, to the N-unsubstituted azetidinone and the latter N-alkylated to nocardian type antibiotics or to the antibiotic substance "PS-5" by using the procedures described by Kametani, T. et al., *Heterocyclics*, 1982, 19, 1023, and Kametani, T., *Heterocyclics* 1982, 17, 463, 479 for carbapenem synthesis via N-substituted methylazetidin-2-ones.

Clavulanic acids and analogs thereof may be obtained with compounds of the invention by the methods described by Bently, P. H. et al., in "Recent Advances in the Chemistry of $\beta$-Lactam Antibiotics", 1981, p. 175, *Tetrahedron Letters* 1979, 1889 and, also Parker, R. M. et al., *J. Chem. Soc. Chem. Commum.*, 1977, 905, 906. 1-Oxapenams (oxabisnorpenicillins) may be made with compounds of the invention by conversion by known methods to the starting materials employed by Cama, L. D. et al., *Tetrahedron Letters*, 44, 4233 in preparing the 1-oxapenams.

Certain of the compounds of the invention are useful intermediates for preparing the 3-acylamino-2-azetidinones described above. For example, when R in the formula 1 is the 3-protected-amino or the 3-amino group, the compounds represented are useful in the preparation of the 3-acylamino-substituted azetidinone antibacterials.

For example, the protecting group of the amino-protected $\beta$-lactam is removed to provide the 3-amino-$\beta$-lactam. The latter nucleus compound is taken acylated by employing acylation methods commonly used to acylate other $\beta$-lactam nucleus compounds e.g. 6APA and 7ACA. Such methods include the use of an active derivative of the carboxylic acid acylating moiety such as the acid halides, and active esters. Active esters such as those prepared with the acid and methyl chloroformate or isobutyl chloroformate, or with the N-hydroxy heterocyclics such as N-hydroxybenzotriazole, and N-hydroxysuccinimide can be used. It will be appreciated that during the acylation of a 3-amino-2-azetidinone compound any free carboxy or other amino groups in the molecule are protected by conventional means.

For example, N-(diphenylmethoxycarbonylmethyl)-3-amino-2-azetidinone is reacted in THF-water with phenoxyacetyl chloride in the presence of triethylamine to provide N-(diphenylmethoxycarbonylmethyl)-3-phenoxyacetamido-2-azetidinone. Treatment of the product with trifluoroacetic acid in the presence of anisole removes the diphenylmethyl ester group to provide the N-(carboxymethyl)azetidinone.

Acylation of N-[(dimethoxycarbonyl)methyl]-3-amino-4-benzyloxycarbonyl-2-azetidinone with N-t-Boc protected-D-phenylglycine in the form of the active ester formed with isobutyl chloroformate provides after deblocking the $\alpha$-amino group and the $C_4$ carboxy group, N-[(dimethoxycarbonyl)methyl]-3-D-phenylglycylamino-4-carboxy-2-azetidinone. – Saponification forms the N-(carboxymethyl) compound.

The compounds of the invention wherein Y is a dialkoxycarbonylmethyl group are converted to compounds wherein Y is carboxymethyl by saponification under mild conditions. When de-esterification to the N-dicarboxymethyl compound occurs decarboxylation results to form the N-carboxymethyl substituted 2-azetidinone.

The compounds of formula 1 wherein $R_2$ is sulfhydryl, $C_1$–$C_4$ alkylthio, $C_2$–$C_4$ alkanoylthio or halo, are prepared after cyclization with compounds of the formula 1 wherein $R_2$ is group convertable by known methods to halo, for example the carboxy group. The halo-substituted compound then can be converted to the —SH, —S-alkyl, or —S-alkanoyl group.

The following examples are provided to further illustrate the invention. In the examples melting points were taken on a Thomas-Hoover melting point apparatus and are uncorrected. Infrared spectra were recorded on a Perkin-Elmer 727b spectrometer. NMR spectra were obtained in chloroform-d with tetramethylsilane as a reference, unless otherwise stated, on a Varian EM390, XL-100 or Nicolet NB300 Spectrometer. Mass spectra were recorded on an AEI Scientific Apparatus 902 or Dupont DP102 spectrometer. High pressure LC was performed using a Beckman/Altex Model 332 chromatograph. Medium pressure chromatography was executed with the Michel-Miller system packed with Silica Gel 60 (40–63$\mu$).

The following abbreviations used in the examples are as follows: DEAD=diethylazodicarboxylate; DIAD=diisopropylazodicarboxylate; THF=tetrahydrofuran; DMF=dimethylformamide; Cbz=carbobenzoxy (benzyloxycarbonyl); IPA=isopropyl alcohol; TPP=triphenylphosphine; LDA=lithium diisopropylamide; Ox refers to the amino-protecting group

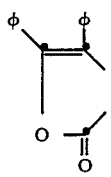

General procedures for the preparation of dipeptides.

Method A. The amino-protected amino acid, 2 eq. of N-hydroxybenzotriazole (HBT), ca. 1.2 eq. of the amine hydrochloride and 1 eq. of triethylamine were dissolved in methylene chloride or DMF. Dicyclohexylcarbodiimido DCC (ca. 1.2 eq) was added and the reaction mixture stirred for about 4 hours to about 20 hours. The insoluble dicyclohexylurea was separated by filtration and the filtrate diluted with diethylether or with ethyl acetate. The solution was washed with 10% sodium carbonate, 0.1N hydrochloric acid, water (only when DMF was the solvent), brine, and then dried over magnesium sulfate. The product was isolated after evaporation, chromatography (where necessary) and recrystallization.

Method B. Alternatively, the water and methylene chloride soluble carbodiimide, 1-cyclohexyl-3-(2-morpholinoethyl)carbodiimide metho-p-toluene-sulfonate (Aldrich) was used instead of DCC. Since the urea produced was water soluble, no chromatographic purification was necessary.

EXAMPLE 1

N-(Methoxycarbonylmethyl)-3-phthalimido-2-azetidinone

Methyl (L)-$N^\alpha$-phthaloylserylglycinate was prepared from (L)-N-phthaloylserine and methyl glycine by method A in 50% yield and isolated as a foamy residue which was homogenous by TLC [75/25 ethyl acetate and hexanes]. NMR 3–3.4 (1H, br), 3.73 (3H, s), 3.84–4.6 (3H, m), 4.9–5.06 (1H, m), 7.6–8.0 (5H, m).

The phthaloylserylglycinate ester (0.66 g, 2.16 mmoles) was treated with 0.57 g (2.18 mmoles) of TPP and 0.34 mL (2.16 mmoles) of DEAD in 30 mL of THF for 3 hours. NMR of the crude mixture showed starting material, the title compound and the dehydropeptide in a ratio of 2:5:3. Chromatography [silica, 80/20 hexanes and ethyl acetate] gave two fractions containing the products. From fraction 2 was crystallized 75.4 mg (0.26 mmoles) of the title compound. M.P. 178°–180° C. IR (HCCl$_3$) 1785 (sh), 1770, 1750, 1720. MS m/e 290 (M+1). Homogenous by HPLC [10μ silica, 250×3.2 mm, 0.4% IPA in methylene chloride, 5 mL/min, 0.25 cm/min, Rt 9.6 min.] NMR 3.83 (3H, s), 3.86–3.98 (2H, m), 3.99–4.5 (2H, q. $J_{CH_2}$=16.5), 5.53–5.6 (1H, dd), 7.6–7.9 (4H, m).

Analysis calculated for $C_{14}H_{12}N_2O_5$: C, 58.13; H, 4.15; N, 9.69 Found: C, 58.31; H, 4.05; N, 9.67.

Fraction 3 contained a mixture of the desired title compound and the dehydropeptide and was re-chromatographed on a TLC column [80/20/0.8 methylene chloride, hexanes, IPA]. 63 mg (0.22 mmoles) of the β-lactam title compound was isolated, but the dehydropeptide composed on the column. The total yield of the title compound was 22%.

EXAMPLE 2

N-[Di-(ethoxycarbonyl)methyl]-3-phthalimido-2-azetidinone

Diethyl (L)-N-phthaloylserylaminomalonate was prepared (method A) in 64% yield. M.P. 103°–105° C. (ethyl acetate and hexanes). NMR 1.17–1.37 (6H, dt), 3.1–3.3 (1H, m), 4.0–4.5 (6H, m), 4.93–5.07 (1H, m), 5.12–5.2 (1H, d), 7.6–8 (5H, m).

Analysis calculated for $C_{18}H_{20}N_2O_8$: C, 55.1; H, 5.1; N, 7.12. Found: C, 54.97; H, 5.22; N, 7.12.

The seryl-aminomalonate dipeptide (0.5 g, 1.28 mmoles) was treated with 0.34 g (1.28 mmoles) of TPP and 0.20 mL (1.28 mmoles) of DEAD in 40 mL of THF for 1.5 hours. The reaction was followed by HPLC and TLC, and shown to be complete in 15 minutes. The title compound and the corresponding dehydropeptide co-eluted on silica gel chromatography [9:1 methylene chloride and ether]. The desired β-lactam (title compound) crystallized selectively from ethyl acetate and hexanes to give 0.2473 g (0.67 mmoles, 52%). M.P. 149°–150° C. IR (KBr) 1780, 1760, 1730. MS (CI with methane) m/e 375 (M+1). NMR 1.19–1.39 (6H, dt) 4.03–4.47 (6H, m), 5.37 (1H, s), 5.47–5.57 (1H, m), 7.6–7.9 (4H, m). $^{13}$C NMR: 15.81, 48.2, 55.8, 58.52, 64.3, 125.3, 133.4, 136.0, 165.9, 166.3, 166.9, 168.2. Single peak by HPLC [10μ silica, 250×3.2 mm, 5 mL/min, 0.25 cm/min, Rt 6.48 min., 898:100:2 methylene chloride, hexanes, IPA].

Analysis calculated for $C_{18}H_{18}N_2O_7$: C, 57.75; H, 4.81; N, 7.49. Found: C, 57.44; H, 5.04; N, 7.38.

The supernatant from the crystallization was enriched in the dehydropeptide side product but it could not be crystallized selectively. HPLC conditions the same as for title compound Rt 6 minutes NMR 1.19–1.39 (6H, dt), 4.0–4.4 (4H, m), 5.17–5.27 (1H, d), 5.93 (1H, m), 6.3 (1H, m), 7.0–7.2 (1H, br d), 7.6–7.9 (4H, m).

EXAMPLE 3

N-[Di-(ethoxycarbonyl)methyl]-3-benzyloxycarbonylamino-2-azetidinone

Diethyl (L)-$N^\alpha$-Cbz serylaminomalanate was prepared (method B) from (L)-N-Cbz-serine and diethyl aminomalonate in 75% yield. M.P. 85°–88° C. (dec.). NMR 1.1–1.3 (6H, m), 3.6–4.5 (8H, m), 5.06 (2H, s), 5.13–5.23 (1H, d), 7.3 (5H, s and 1H, br.).

Analysis calculated for $C_{18}H_{24}N_2O_8$: C, 54.54; H, 6.06; N, 7.07. Found: C, 54.40; H, 6.04; N, 7.15.

The Cbz protected serylaminomalonate (0.5 g, 1.2 mmoles) and 0.33 g (1.2 mmoles) of TPP in 30 mL of THF were treated with 0.2 mL (1.29 mmoles) of DEAD for 1 hour at R.T. The mixture was chromatographed as above, yielding 0.29 g (63% mass recovery) of the mixture of the title compound and 1-Cbz-2-carboxyaziridine diethoxycarbonylmethylamide. 105 mg of the mixture was prep TLC'd (silica, 2 mm, ether/hexanes, 4 times). The title compound eluted first, and after evaporation, 64.1 mg (0.18 mmoles, 15%) was isolated as an oil. IR (neat) 1770, 1750, 1715. NMR 1.13–1.33 (6H, m), 3.56–3.7 (2H, m), 4.0–4.4 (4H, m), 4.6–4.8 (1H, m), 5.1 (3H, 2 overlapping singlets), 5.8–6 (1H, m), 7.4 (5H, s). The aziridine side product: 39.5 mg (0.1 mmoles, 8.7%) IR (neat) 1760, 1730. NMR 1.16–1.33 (6H, t), 2.4–2.6 (2H, dd), 3.06–3.16 (1H, dd), 4.1–4.4 (4H, dq), 4.5–4.8 (1H, b), 5.06–5.1 (1H, d), 5.13 (2H, s), 7.4 (5H, s).

EXAMPLE 4

N-[Di-(ethoxycarbonyl)methyl]-3,3-dimethyl-2-azetidinone

Diethyl N(β-hydroxypivaloyl)aminomalonate was prepared (method B) from β-hydroxy pivalic acid and diethyl aminomalonate in 88% yield. The compound was isolated as an oil. NMR 1.13–1.3 (12H, m), 3.5 (2H, br s), 4.16–4.4 (4H, q), 5.1–5.16 (1H, d), 7.6–7.7 (1H, d).

The β-hydroxypivaloylaminomalonate (0.5 g, 1.8 mmoles) and 0.5 g (1.9 mmoles) of TPP were dissolved in 20 ml of THF. 0.33 mL (1.9 mmoles) of DEAD was added dropwise under nitrogen. After 1 hour the mixture was concentrated and chromatographed (silica, methylene chloride and hexanes) to yield 0.499 g of an oil. Crystallization from hexanes gave 0.27 g (0.64 mmoles, 35%) of the adduct represented by the formula

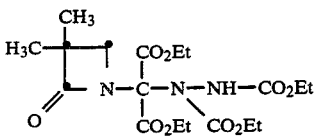

M.P. 68°–69° C. IR 1760, (shoulders at 1740, 1720). NMR 1.16–1.4 (18H, m), 3.6 (2H, bs), 4.06–4.43 (8H, overlapping quartets), 7.1–7.3 (1H, bs).

Analysis calculated for $C_{18}H_{24}N_3O_9$: C, 50.1; H, 6.70; N, 9.7. Found: C, 50.08; H, 6.70; N, 9.73.

The mother liquor contained exclusively the β-lactam title compound which was isolated as an oil. IR (neat) 1780, 1740. NMR 1.16–1.36 (12H, singlet overlapping a triplet), 3.4 (2H, s), 4.13–4.4 (4H, q), 5.16 (1H, s).

EXAMPLE 5

N-[(Diethylaminocarbonyl)methyl]-3,3-dimethyl-2-azetidinone via diethyl N-(β-chloropivaloyl)aminomalonate Diethyl aminomalonate hydrochloride (1 g, 4.7 mmole) was dissolved in 5 mL of dry pyridine and cooled to 0° C. β-Chloropivaloylchloride (0.72 g, 4.7 mmole) was added dropwise under nitrogen. The mixture was warmed to room temperature and stirred for 2 hours at which time 50 mL of anhydrous ether was added. The precipitate was filtered and the supernatant washed with 0.1N HCl (4×25 mL), 5% $NaHCO_3$ (25 mL), brine (50 mL) and dried over $MgSO_4$. On evaporation, 1.35 g (4.6 mmoles, 98%) of the oily product was isolated. NMR 1.16–1.33 (12H, m), 3.63 (2H, s), 4.13–4.36 (4H, q), 5.06–5.13 (1H, d), 6.8–6.9 (1H, bd).

A. Cyclization with 100 Mole % of Base

The N-(β-chloropivaloyl)aminomalonate ester (0.5 g, 1.7 mmoles) was treated with 75 mg (1.7 mmoles) of pre-washed 50% NaH in 10 mL of DMF/methylene chloride (1:4) for 15 hours under $N_2$. The reaction was quenched in 0.1N HCl and extracted with ethyl acetate (100 mL). The organic phase was then washed with 0.1N HCl (25 mL), $H_2O$ (2×25 mL), brine (25 mL) and dried over $MgSO_4$. Evaporation, followed by recrystallization from hexanes gave a total of 0.203 g (0.70 mmoles, 46%) of 3,3-dimethyl-5,5-diethyloxycarbonyl-pyrrolidone-2, IR (KBr), 1720, 1700; NMR 1.13–1.3 (12H, m), 2.53 (2H, s), 4.0–4.4 (4H, m), 6.6 (1H, b).

Analysis calculated for $C_{12}H_{19}NO_5$: C, 56.03; H, 7.39; N, 5.45. Found: C, 56.18; H, 7.56; N, 5.45.

B. Cyclization with 220 Mole % of Base

The β-chloropivaloylaminomalonate (155 mg, 0.53 mmole) was dissolved in 6 mL of THF and cooled to −78° C. under $N_2$. LDA (220 mole % from 0.167 mL, 1.2 mmole, of diisopropyl amine and 1 mL of 1.3M n-BuLi in 3 mL of THF) was added. The light yellow solution of the dianion was allowed to warm slowly to room temperature over 4–5 hours. After continued stirring for 12 hours, the solution was diluted with 75 mL of ether and washed with 25 mL of 0.1N NCl, 25 mL of 5% $NaHCO_3$, and 25 mL of brine. Drying over $MgSO_4$, filtering, and evaporation yielded 114.4 mg (0.45 mmole, 84%) of the β-lactam title compound of which was identical to that prepared as described by Example 4.

EXAMPLE 6

N-(3-Ethoxycarbonylpropen-2-yl)-3,3-dimethyl-2-azetidinone

Ethyl N-(β-chloropivaloyl)-3-aminocrotonate was prepared in 42% yield from β-chloropivaloyl chloride and ethyl 3-aminocrotonate by the procedure used in Example 5. M.P. 76°–77.5° C. (after recrystallization from hexanes); IR (KBr) 1705, 1675 $cm^{-1}$; 'HNMR δ 1.06–1.23 (9H, m), 2.3 (3H, s), 3.6 (2H, s), 4.0–4.23 (2H, q) 6.7 (1H, s), 6.8–7.1 (1H, br).

Analysis calculated for $C_{11}H_{18}NO_3Cl$: C, 53.44; H, 7.29; N, 5.67. Found: C, 53.10; H, 7.20; N, 5.73.

The β-chloropivaloyl amide cyclization to the title β-lactam compound was accomplished by treatment of 209 mg (0.84 mmole) of the amide with 64.5 mg (1.3 mmole) of NaH in 5 mL of DMF-$CH_2Cl_2$ (1:4) for 3 hours at room temperature. The reaction mixture was poured into 75 mL of ether and washed with two 25 mL portions of water, 25 mL of brine, dried over $MgSO_4$, filtered and evaporated to yield 177 mg (0.84 mmole, 100%) of the β-lactam title compound as an oil. IR (neat) 1770, 1705 $cm^{-1}$; $^1H$ NMR δ 1.16–1.33 (9H, m), 2.63 (3H, s), 3.26 (2H, s), 4.03–4.26 (2H, q), 5.2 (1H, s).

EXAMPLE 7

N-(2-Methyl-1-ethoxycarbonylpropen-1-yl)-3,3-dimethyl-2-azetidinone

Ethyl N-(β-chloropivaloyl)dehydrovaline was prepared in 20% yield by the procedure used in Examples 5 and 6. M.P. 111°–113° C.; IR (KBr) 1715, 1640; 'HNMR δ 1.13–1.36 (3H, t and 6H, s), 1.83 (3H, s), 2.2 (3H, s), 3.67 (2H, s), 4.1–4.3 (2H, q), 6.9–7.2 (1H, br s).

Analysis calculated for $C_{25}H_{20}NO_3Cl$: C, 55.17; H, 7.66; N, 5.36. Found: C, 55.02; H, 7.65; N, 5.47.

The dehydrovalineamide was cyclized to the β-lactam title compound in the same manner as described in Example 6. The title compound represented by the formula

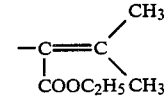

was obtained as an oil in 83% yield. IR (thin film in $CDCl_3$) 1760, 1740, 1720 $cm^{-1}$. $^1H$ NMR δ 1.23–1.37 (3H, t and 6H, s); 1.93 (3H, s), 2.23 (3H, s), 3.3 (2H, s), 4.09–4.3 (2H, q).

EXAMPLE 8

Diethyl-3(S)-amino-1-malonyl-2-azetidinone

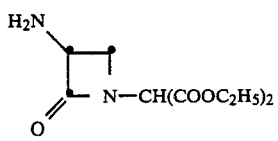

Diethyl N$^\alpha$-Ox-L-serylaminomalonate was prepared in 59% yield by method B using N-Ox-L-serine DCHA salt and diethyl aminomalonate. M.P. 104°–105° C. (after recrystallization from ethyl acetate-hexanes); NMR δ 1.1–1.35 (6H, m), 4.0–4.35 (8H, m), 5.1–5.2 (1H, d), 7.3 (5H, s), 7.5 (5H, s), 8.1–8.15 (1H, brd); $[\alpha]_D^{23} = 13.4$ (d=0.73, CH$_3$OH).

Analysis calculated for C$_{25}$H$_{26}$N$_2$O$_8$: C, 62.24; H, 5.39; N, 5.81. Found: C, 61.89; H, 5.48; N, 5.87.

To 25 mL of dry THF was added 1.1 g (2.5 mmole) of the Ox protected seryl amide and 0.78 g (3 mmole) of TPP. While stirring at room temperature, a solution of 0.5 mL (2.5 mmole) of DIAD in 25 mL of THF was added dropwise over 1 hour. Immediately after completion of the addition, the colorless solution was concentrated and chromatographed (silica gel, CH$_2$Cl$_2$) to provide 1.1 g (2.45 mmole, 96%) of the desired β-lactam title compound. M.P. 94°–95° C. (after recrystallizing from ethyl acetate-hexanes); $[\alpha]_D^{23} = -70.2°$ (C=0.97, CH$_3$CH$_2$OH); $^1$H NMR δ 1.17–1.40 (6H, m), 3.87–4.4 (6H, m), 4.87–5.0 (1H, dd), 5.17 (1H, s), 7.26 (5H, s), 7.47–7.60 (5H, m); IR (KBr), 1730–1790 cm$^{-1}$ (br, C=O).

Analysis calculated for C$_{25}$H$_{24}$N$_2$O$_7$: C, 64.65; H, 5.17; N, 6.03. Found: C, 65.28; H, 5.35; N, 6.07.

The 3-amino title compound was prepared by catalytic hydrogenation of 324 mg (0.72 mmole) of the Ox protected 3-amino β-lactam in 15 mL of ethanol containing 0.6 mL of 1.2N HCl over 80 mg of 10% Pd-C at 35 psi for 4.5 hours. The mixture was then filtered through Celite. The Celite was washed with 50 mL of ethanol and the combined filtrate was evaporated. The residue was recrystallized from ethanol-ether to give 165.4 mg (0.59 mmole, 82%) of title compound. M.P. 137°–141° (d); $[\alpha]_D^{23} = -33.8$ (C=0.4, ethanol; $^1$H NMR δ 1.16–1.37 (6H, t), 3.93–4.4 (6H, m), 4.67–4.9 (1H, m), 5.3 (1H, s), 8–10 (3H, br). IR (KBr) 1780–1730 cm$^{-1}$ (br C=O).

Analysis calculated for C$_{10}$H$_{17}$N$_2$O$_5$Cl: C, 42.86; H, 6.07; N, 10.0. Found: C, 42.88; H, 6.16; N, 10.07.

EXAMPLE 9

N-[Di-(ethoxycarbonyl)methyl]-3-amino-4-methyl-2-azetidinone

L-Threonine (5 g, 42 mmoles) was mixed with 18 mL of benzyltriethylammonium hydroxide (40% in methanol). After evaporating three times from ethanol (100 mL), the resulting oil was taken up in DMF (50 mL) and treated with 1,2-diphenylvinylene carbonate (10 g) for 4 hours. The mixture was acidified with 1.2N HCl (40 mL) and extracted with ethyl acetate (200 mL). The organic layer was washed with water (3×100 mL), brine (100 mL), and dried over MgSO$_4$. The residue left after evaporation was taken up in 40 mL of TFA and stirred for 3 hours. The TFA was removed in vacuo and the residue was vacuum desicated for 12 hours. The crude product was taken up in ethyl acetate (200 mL) and washed with water (5×50 mL), brine (100 mL), and dried over Na$_2$SO$_4$. After reducing the volume of ethyl acetate to ⅓, 100 mole % of dicyclohexylamine, (DCHA) was added. On standing the Ox-protected threonine DCHA salt crystallized. 13.8 g (26.5 mmoles, 63%) in three crops. M.P. 190°–192° C. (ethanol-ether). NMR (DCCl$_3$/DMSO-d$_6$): 0.99–2.16 (23H, m); 2.7–3.2 (2H, br m); 3.7–3.76 (1H, d, J=6 Hz); 4.27–4.5 (2H, br m); 7.2 (5H, s); 7.3–7.6 (5H, br m).

Ox-L-Threonine DCHA salt (2 g, 3.85 mmoles), N-hydroxybenzotriazole (0.57 g, 4.3 mmoles) and diethylaminomalonate hydrochloride (0.9 g, 4.2 mmoles) were dissolved in 50 mL of methylene chloride. 1-Cyclohexyl-3-(2-morpholinoethyl)carbodiimide metho-p-toluenesulfone (1.8 g, 4.3 mmoles) was added and the reaction stirred for 6 hours at R.T. On diluting with 100 ml. of ethyl acetate, the mixture was washed with 0.18M H$_2$SO$_4$ (2×50 mL), 10% Na$_2$CO$_3$ (3×25 mL), brine (50 ml), and dried over MgSO$_4$. The residue obtained after evaporation was chromatographed (silica, 9:1 methylene chloride to ether), yielding 0.9137 g (1.84 mmoles, 47% of the N-diethoxycarbonylmethyl)amide. NMR (DCCl$_3$): 1.06–1.37 (9H, m); 3.87–3.93 (1H, d, J=6 Hz); 4.13–4.37 (4H, q); 3.67–4.77 (2H, br m); 5.07–5.13 (1H, d); 7.23 (5H, s); 7.33–7.5 (5H, br m); 8.1–8.25 (1H, br d).

Ox-L-Threonylaminomalonate (0.45 g, 0.92 mmoles) and TPP (0.26 g, 0.1 mmoles) were dissolved in THF (15 mL). DIAD (0.196 mL, 0.1 mmoles) in THF (15 mL) was added dropwise over 0.5 hour, after which the reaction mixture was evaporated and chromatographed (silica, 9:1 methylene chloride to ether). A mixture (0.32 g) containing the product was eluted. By NMR this mixture contained the desired β-lactam along with the dehydropeptide and the pyrrolidinone. The ratio of products (73%) was roughly 2:1:1. Careful rechromatography (slower gradient) led to the isolation of the β-lactam 50 mg (0.1 mmoles, 11%); M.P. 140°–142° C. NMR (DCCl$_3$): 1.16–1.14 (9H, m); 4.09–4.5 (7H, m); 5.13 (1H, s); 7.23 (5H, s); 7.3–7.66 (5H, m).

The Ox protecting group is removed by catalytic hydrogenolysis of the cyclized product in ethyl alcohol using 10% palladium on carbon under about 35 psi of hydrogen to provide diethyl-3(S)-amino-1-malonyl-4-methyl-2-azetidinone represented by the formula

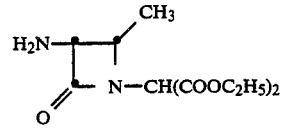

EXAMPLE 10

N-[Di(ethoxycarbonyl)methyl]-3R-tert-butyloxycarbonylamino-4-R-methoxycarbonyl-2-azetidinone, 3R L-Erythro-β-hydroxyaspartic acid (1 g., 6.7 mmoles) was dissolved in 15 ml. of methyl alcohol containing 1.1 ml. of concentrated hydrochloric acid and the solution was heated at the reflux temperature for 3 hours. On cooling the reaction mixture was evaporated to dryness and the residue desicated in vacuo. The solid product was triturated with diethyl ether and filtered to give 1.32 g (99%) of methyl β-hydroxyaspartic acid hydrochloride melting at about 182° C. to about 183° C.

The ester hydrochloride (600 mg., 3.0 mmoles) was dissolved in 15 ml. of THF-water (1-1) containing 660 mg. (3.0 mmoles) of t-butylpyrocarbonate and 1.25 ml. (9.0 mmoles) of triethylamine. After 1.5 hours the reaction mixture was extracted with 25 ml. of ethyl acetate and then acidified to pH 2 with cold 6N hydrochloric acid. The acidified mixture was extracted further with three 50 ml. portions of ethyl acetate. The extracts were combined, washed with 50 ml. of brine, dried over mangesium, sulfate, filtered, and concentrated by evaporation to give 632 mg (2.4 mmoles, 80%) of methyl N-BOC-L-erythro-$\beta$-hydroxyaspartic acid. NMR (CDCl$_3$): 1.46 (s, 9H), 3.8 (s, 3H), 4.53 (d, 1H), 4.8–4.9 (br d, 1H), 5.73–5.8 (br d, 1H), and 6.9–7.1 (br s, 2H).

The t-BOC protected ester is converted (method B) to the amide formed with diethylaminomalonate represented by the formula

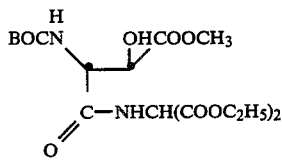

and the amide reacted with TPP and diisopropylazodicarboxylate to provide the title compound.

EXAMPLE 11

N-(Sulfomethyl)-3-(4,5-diphenyl-2-oxo-4-oxazolino)-2-azetidinone.

Ox-protected-2-serine is coupled with aminomethanesulfonic acid tetra-n-butylammonium salt in tetrahydrofuran to provide the amide represented by the formula

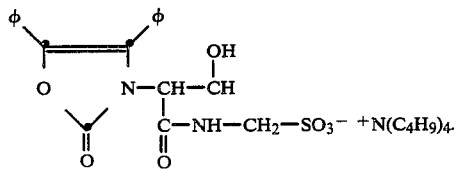

The amide is cyclized with TPP and diisopropylazodicarboxylate to provide the 3-(Ox-protected)-N-(sulfomethyl)-2-azetidinone.

I claim:
1. A compound of the formula

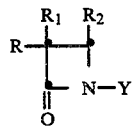

wherein
R is hydrogen, C$_1$–C$_4$ alkoxy, C$_1$–C$_4$ alkyl, C$_1$–C$_4$ alkyl mono-substituted by hydroxy, C$_1$–C$_4$ alkoxy, halogen, amino, protected-amino, carboxy, or protected carboxy; or R is amino, or protected amino wherein the protecting group is C$_1$–C$_5$ alkanoyl, C$_1$–C$_5$ alkanoyl mono-substituted by halogen, cyano, or hydroxy; an arylacetyl or heteroarylacetyl group of the formula

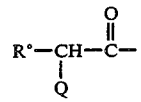

wherein
R° is thienyl, benzothienyl, furyl, benzofuryl, thiazolyl, oxazolyl, isoxazolyl, isothiazolyl, pyrazolyl, thiadiazolyl, oxadiazolyl, pyridyl, and said heterocyclic rings mono-substituted by C$_1$–C$_4$ alkyl, amino, protected amino, or hydroxy; cyclohexadienyl, naphthyl, phenyl, or a substituted phenyl group of the formula

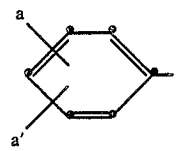

wherein a and a' independently are hydrogen, halogen, hydroxy, C$_1$–C$_4$ alkyl, C$_1$–C$_4$ alkoxy, amino, aminomethyl, methylsulfonylamino, hydroxymethyl, trifluoromethyl, carboxy, protected carboxy, carboxymethyl, or protected carboxymethyl;

Q is hydrogen, hydroxy, C$_1$–C$_4$ alkanoyloxy, carboxy, protected carboxy, sulfo (—SO$_3$H), amino, protected amino, or a substituted amino group of the formula

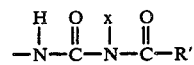

wherein
x is hydrogen or C$_1$–C$_3$ alkyl; R' is furyl, thienyl, phenyl, halophenyl, nitrophenyl, styryl, halostyryl, nitrostyryl, or a group of the formula

wherein
y is hydrogen or C$_1$–C$_3$ alkyl; R" is hydrogen, C$_1$–C$_4$ alkyl, benzyl, C$_2$–C$_5$ alkanoyl, or C$_1$–C$_3$ alkylsulfonyl; and when R' is —N(y)R" x and y may be taken together with the —N—C(O)—N—R" group to which they are bonded to form a 5- or 6-membered ring-containing group of the formula

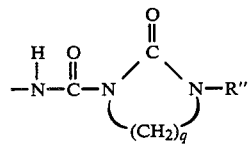

wherein
R" has the same meanings as defined hereinabove and q is 2 or 3;
or Q is a substituted amino group of the formula

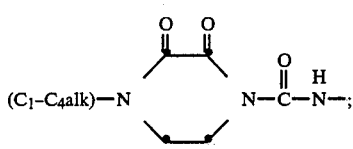

or Q is a benzamido group of the formula

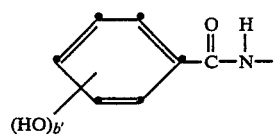

wherein
b' is an integer of 1–3;
or R is an acylamino group of the formula

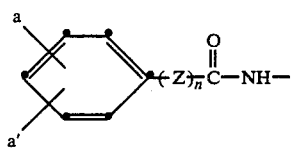

wherein
a and a' have the same meanings as defined above, Z is O or S, and n is 0 or 1; or an oximino-substituted acylamino group of the formula

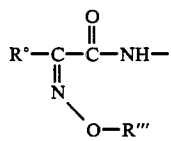

wherein
R° is as defined above, and R''' is hydrogen, $C_1$–$C_4$ alkyl, or a carboxy-substituted alkyl or carboxy-substituted cycloalkyl group of the formula

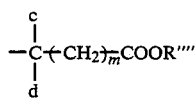

wherein
m is 0 to 3, and c and d when taken separately are independently hydrogen or $C_1$–$C_3$ alkyl, and when taken together with the carbon atom to which they are bonded form a 3- to 6-membered carbocyclic ring; and R'''' is hydrogen, or a carboxy-protecting ester group;
$R_1$ is hydrogen, hydroxy, $C_1$–$C_4$ alkoxy, halogen, or $C_1$–$C_4$ alkyl;
$R_2$ is hydrogen;
Y is a substituted methyl group of the formula

wherein
$R_3$ is protected carboxy; and $R_4$ is hydrogen, or a carboxy-protecting group.

2. The compound of the formula

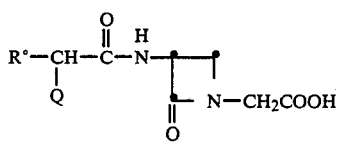

wherein
R° is thienyl, benzothienyl, furyl, benzofuryl, thiazolyl, oxazolyl, isoxazolyl, isothiazolyl, pyrazolyl, thiadiazolyl, oxadiazolyl, pyridyl, and said heterocyclic rings mono-substituted by $C_1$–$C_4$ alkyl, amino, protected amino, or hydroxy; cyclohexadienyl, naphthyl, phenyl, or a substituted phenyl group of the formula

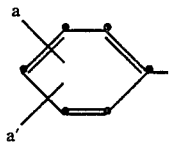

wherein
a and a' independently are hydrogen, halogen, hydroxy, $C_1$–$C_4$ alkyl, $C_1$–$C_4$ alkoxy, amino, aminomethyl, methylsulfonylamino, hydroxymethyl, trifluoromethyl, carboxy, protected carboxy, carboxymethyl, or protected carboxymethyl;
Q is a substituted amino group of the formula

wherein
x is hydrogen or $C_1$–$C_3$ alkyl; R' is furyl, thienyl, phenyl, halophenyl, nitrophenyl, styryl, halostyryl, nitrostyryl, or a group of the formula

wherein
y is hydrogen or $C_1$–$C_3$ alkyl; R'' is hydrogen, $C_1$–$C_4$ alkyl, benzyl, $C_2$–$C_5$ alkanoyl, or $C_1$–$C_3$ alkylsulfonyl; and when R' is —N(y)R'' x and y may be taken together with the —N—C(O)—N—R'' group to which they are bonded to form a 5- or 6-membered ring-containing group of the formula

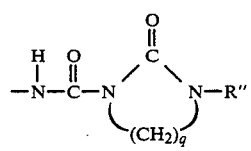

wherein
R'' has the same meanings as defined hereinabove and q is 2 or 3;
or Q is a substituted amino group of the formula

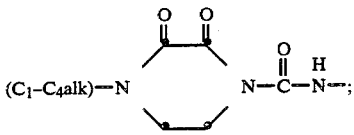

or Q is a benzamido group of the formula

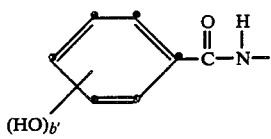

wherein
b' is an integer of 1–3.

3. The compound of the formula

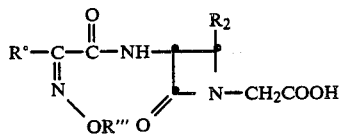

wherein
R° is thienyl, benzothienyl, furyl, benzofuryl, thiazolyl, oxazolyl, isoxazolyl, isothiazolyl, pyrazolyl, thiadiazolyl, oxadiazolyl, pyridyl, and said heterocyclic rings substituted by $C_1$–$C_4$ alkyl, amino, protected amino, or hydroxy; cyclohexadienyl, naphthyl, phenyl, or a substituted phenyl group of the formula

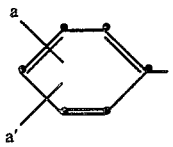

wherein
a and a' independently are hydrogen, halogen, hydroxy, $C_1$–$C_4$ alkyl, $C_1$–$C_4$ alkoxy, amino, aminomethyl, methylsulfonylamino, hydroxymethyl, trifluoromethyl, carboxy, protected carboxy, carboxymethyl, or protected carboxymethyl;
R''' is hydrogen, $C_1$–$C_4$ alkyl, or a carboxy-substituted alkyl or carboxy-substituted cycloalkyl group of the formula

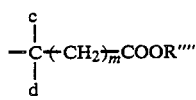

wherein
m is 0 to 3, and c and d when taken separately are independently hydrogen or $C_1$–$C_3$ alkyl, and when taken together with the carbon atom to which they are bonded form a 3- to 6-membered carbocyclic ring; and R'''' is hydrogen, or a carboxy-protecting ester group; and $R_2$ is hydrogen or methyl.

4. The compound of claim 1 wherein R is a group of the formula

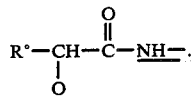

5. The compound of claim 1 wherein R is a group of the formula

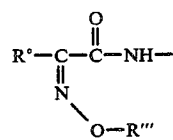

and R''' is $C_1$–$C_4$ alkyl or a carboxy-substituted alkyl group.

6. The compound of claim 3 wherein R° is 2-furyl, 2-thienyl, or 2-aminothiazol-4-yl, and R''' is methyl, carboxymethyl, or 2-carboxyprop-2-yl.

7. The compound of claim 6 wherein R° is 2-aminothiazol-4-yl.

8. The compound of claim 5 wherein R° is 2-aminothiazol-4-yl and R''' is methyl.

9. The compound of claim 8 said compound being syn-N-[(diethoxycarbonyl)methyl]-3-[2-(2-aminothiazol-4-yl)-2-methoxyiminoacetamido]-2-azetidinone.

10. The compound of claim 7 said compound being syn-N-(carboxymethyl)-3-[2-(2-aminothiazol-4-yl)-2-methoxyiminoacetamido]-4-methyl-2-azetidinone.

11. The syn isomer of the compound of claim 6.

12. The compound of the formula

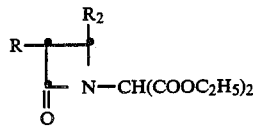

wherein R is benzyloxycarbonylamino, phthalimido, or 4,5-diphenyl-2-oxo-4-oxazolino, and $R_2$ is hydrogen or methyl.

13. The compound of claim 12 of the formula

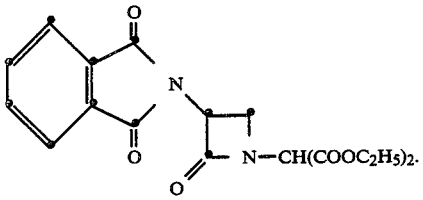

14. The compound of claim 12 of the formula

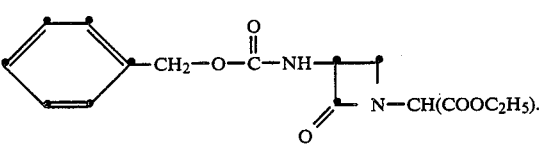

15. The compound of claim 12 of the formula

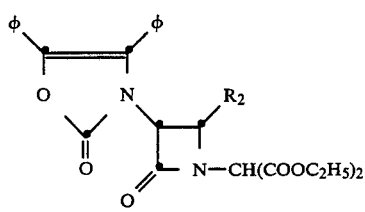
wherein R₂ is hydrogen or methyl.
16. The compound of claim 1 wherein R is amino.
17. The compound of the formula
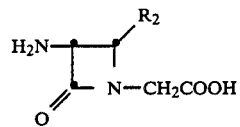
wherein $R_2$ is hydrogen, methyl, or carboxy, and the acid addition salts thereof.
18. The compound of the formula
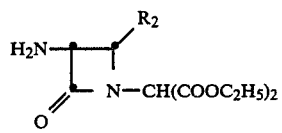
wherein $R_2$ is hydrogen, methyl, or protected carboxy and the acid addition salts thereof.
* * * * *